(12) United States Patent
Suzuki et al.

(10) Patent No.: US 10,379,120 B2
(45) Date of Patent: Aug. 13, 2019

(54) BLOOD ANALYZER AND BLOOD ANALYSIS METHOD

(71) Applicant: Sysmex Corporation, Kobe-shi, Hyogo (JP)

(72) Inventors: Yuhgi Suzuki, Kobe (JP); Nozomu Higuchi, Kobe (JP)

(73) Assignee: SYSMEX CORPORATION, Kobe-Shi, Hyogo (JP)

(*) Notice: Subject to any disclaimer, the term of this patent is extended or adjusted under 35 U.S.C. 154(b) by 511 days.

(21) Appl. No.: 15/081,206

(22) Filed: Mar. 25, 2016

(65) Prior Publication Data

US 2016/0282346 A1   Sep. 29, 2016

(30) Foreign Application Priority Data

Mar. 27, 2015 (JP) .................. 2015-066845

(51) Int. Cl.
| | |
|---|---|
| G01N 33/569 | (2006.01) |
| G01N 33/49 | (2006.01) |
| G01N 33/50 | (2006.01) |
| G01N 15/14 | (2006.01) |
| G01N 1/34 | (2006.01) |
| G01N 15/00 | (2006.01) |
| G01N 15/10 | (2006.01) |

(52) U.S. Cl.
CPC ......... *G01N 33/56972* (2013.01); *G01N 1/34* (2013.01); *G01N 15/1459* (2013.01); *G01N 33/4915* (2013.01); *G01N 33/5094* (2013.01); *G01N 2015/008* (2013.01); *G01N 2015/1006* (2013.01); *G01N 2015/1402* (2013.01); *G01N 2015/1477* (2013.01); *G01N 2015/1486* (2013.01); *G01N 2333/7051* (2013.01); *G01N 2333/70503* (2013.01); *G01N 2333/70514* (2013.01); *G01N 2333/70589* (2013.01); *G01N 2800/56* (2013.01); *Y02A 50/58* (2018.01)

(58) Field of Classification Search
None
See application file for complete search history.

(56) References Cited

U.S. PATENT DOCUMENTS

| | | | | |
|---|---|---|---|---|
| 4,284,412 A * | 8/1981 | Hansen | ............. | G01N 15/1459 |
| | | | | 250/432 R |
| 6,900,023 B1 * | 5/2005 | Houwen | ............ | G01N 33/5094 |
| | | | | 435/2 |
| 2004/0197768 A1 * | 10/2004 | Glencross | .......... | G01N 15/1468 |
| | | | | 435/4 |

FOREIGN PATENT DOCUMENTS

| | | |
|---|---|---|
| CN | 101389947 | 3/2009 |
| CN | 102016573 | 4/2011 |
| EP | 2 293 062 A1 | 3/2011 |
| EP | 2 520 926 A1 | 11/2012 |
| JP | 2001-091513 A | 4/2001 |

(Continued)

*Primary Examiner* — Rebecca L Martinez
(74) *Attorney, Agent, or Firm* — Brinks Gilson & Lione

(57) ABSTRACT

A blood analyzer including a specimen preparation unit, a flow cell, a light source unit, light receivers, and a processing unit. The processing unit is configured to identify and count lymphocytes in the first measurement specimen by using first scattered light information based on the first scattered light and second scattered light information based on the second scattered light, and configured to identify and count blood cells having thereon the predetermined surface antigen in the first measurement specimen by using first fluorescence information based on the first fluorescence.

14 Claims, 11 Drawing Sheets

(56) References Cited

FOREIGN PATENT DOCUMENTS

| JP | 2009-522556 | 6/2009 |
|----|---|---|
| WO | WO 2007/076549 | 7/2007 |
| WO | WO 2009/136570 | 11/2009 |
| WO | WO 2009/136573 | 11/2009 |

\* cited by examiner

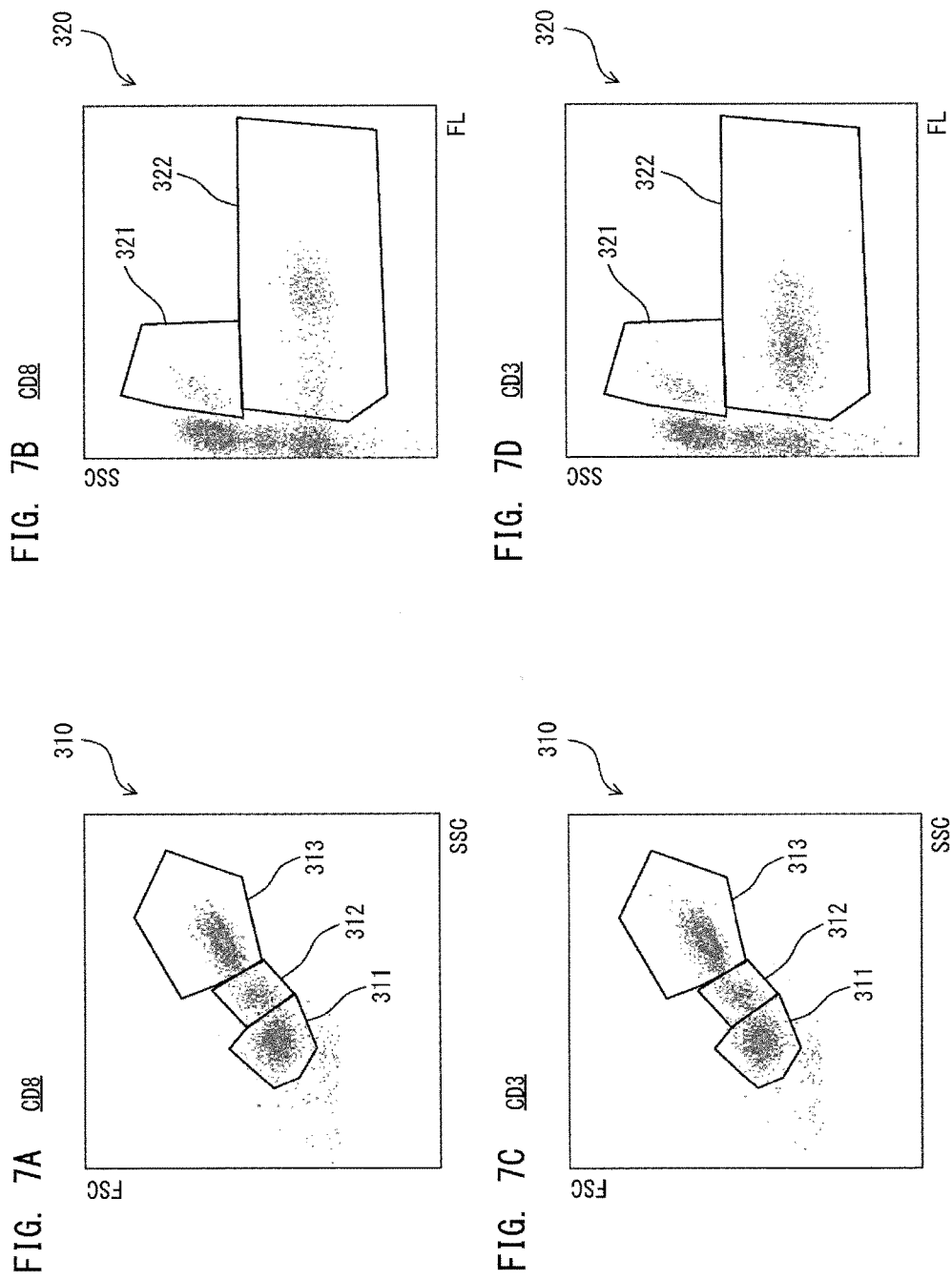

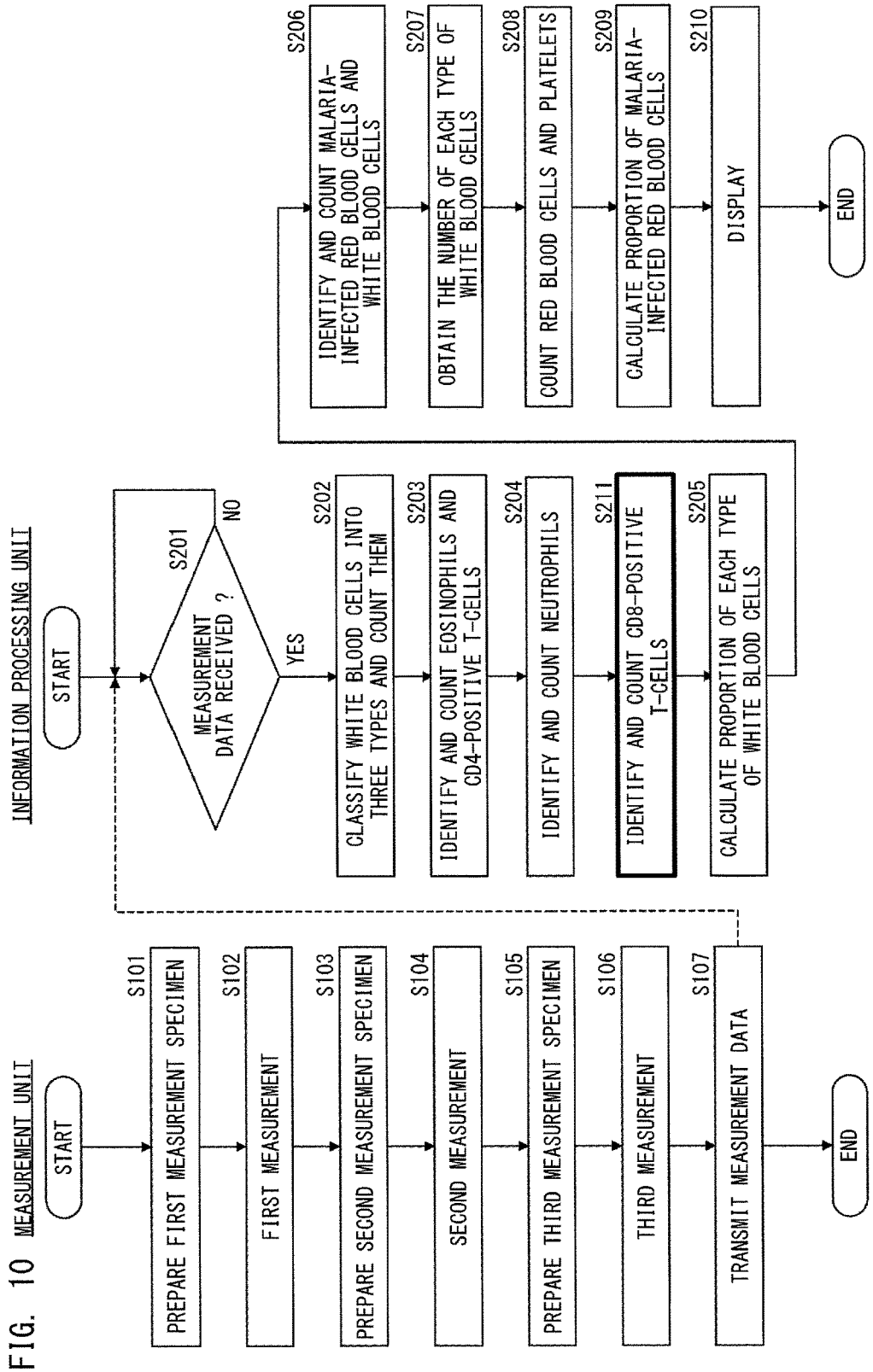

BLOOD ANALYZER AND BLOOD ANALYSIS METHOD

CROSS REFERENCE TO RELATED APPLICATION

This application claims priority from prior Japanese Patent Application No. 2015-066845, filed on Mar. 27, 2015, entitled "BLOOD ANALYZER AND BLOOD ANALYSIS METHOD", the entire content of which is incorporated herein by reference.

FIELD OF THE INVENTION

The present invention relates to blood analyzers and blood analysis methods for counting blood cells in blood samples.

BACKGROUND

Analyzing the state of cell surface antigens included in a blood sample is effective in diagnosis of diseases. For example, in a subject infected with HIV (Human Immunodeficiency Virus), the number of CD4-positive T-cells in blood decreases as the disease condition progresses. On the basis of the number of CD4-positive T-cells in the blood sample, infection with HIV and progress of disease condition thereof can be diagnosed. Japanese Laid-Open Patent Publication No. 2001-91513 describes a method in which: a first fluorescence-labeled antibody for recognizing white blood cells, a second fluorescence-labeled antibody for recognizing an antigen that changes its expression in accordance with the maturity stage of neutrophilic cells, and a third fluorescence-labeled antibody for recognizing an antigen that changes its expression in accordance with the maturity stage of immature granulocytic cells are used, to classify and count immature granulocytes having different degrees of maturity on the basis of scattered light intensity and three types of fluorescence.

With the method described in Japanese Laid-Open Patent Publication No. 2001-91513, it is necessary to prepare various types of fluorescence-labeled antibody reagents for performing classification and counting regarding cell surface antigens. In addition, prior to measurement, an ammonium chloride-based hemolyzing agent is mixed to the blood sample, and the resultant mixture is subjected to centrifugation to remove red blood cells and platelets. Thus, in order to prepare a measurement specimen, complicated pretreatment is necessary. This results in long time and increased cost in performing classification and counting regarding cell surface antigens.

SUMMARY OF THE INVENTION

The scope of the present invention is defined solely by the appended claims, and is not affected to any degree by the statements within this summary.

A blood analyzer according to a first mode of the present invention includes: a specimen preparation unit configured to mix a blood sample with a hemolyzing agent which hemolyzes red blood cells and with a fluorescence-labeled antibody reagent which labels a predetermined surface antigen on blood cells, to prepare a first measurement specimen; a flow cell through which the first measurement specimen prepared by the specimen preparation unit is caused to flow; a light source unit configured to emit light to the first measurement specimen flowing in the flow cell; light receivers configured to respectively receive first scattered light, second scattered light, and first fluorescence which are obtained from blood cells in the first measurement specimen as a result of the emission of the light; and a processing unit configured to identify and count lymphocytes in the first measurement specimen by using first scattered light information based on the first scattered light and second scattered light information based on the second scattered light, and configured to identify and count blood cells having thereon the predetermined surface antigen in the first measurement specimen by using first fluorescence information based on the first fluorescence.

A blood analysis method according to a second mode of the present invention includes the steps of: mixing a blood sample with a hemolyzing agent which hemolyzes red blood cells and with a fluorescence-labeled antibody reagent which labels a predetermined surface antigen on blood cells, to prepare a first measurement specimen; causing the prepared first measurement specimen to flow in a flow cell; emitting light to the first measurement specimen flowing in the flow cell; respectively detecting first scattered light, second scattered light, and first fluorescence which are obtained from blood cells in the first measurement specimen as a result of the emission of the light; identifying and counting lymphocytes in the first measurement specimen by using first scattered light information based on the first scattered light and second scattered light information based on the second scattered light; and identifying and counting blood cells having thereon the predetermined surface antigen in the first measurement specimen by using first fluorescence information based on the first fluorescence.

BRIEF DESCRIPTION OF THE DRAWINGS

FIG. 7A shows a scattergram based on first measurement according to Modification of Embodiment 1;

FIG. 7B shows a scattergram based on the first measurement according to Modification of Embodiment 1;

FIG. 7C shows a scattergram based on the first measurement according to Modification of Embodiment 1;

FIG. 7D shows a scattergram based on the first measurement according to Modification of Embodiment 1;

FIG. 10 is a flow chart showing a process performed by the blood analyzer according to Embodiment 2.

DETAILED DESCRIPTION OF THE PREFERRED EMBODIMENTS

Embodiment 1

Figure 1:
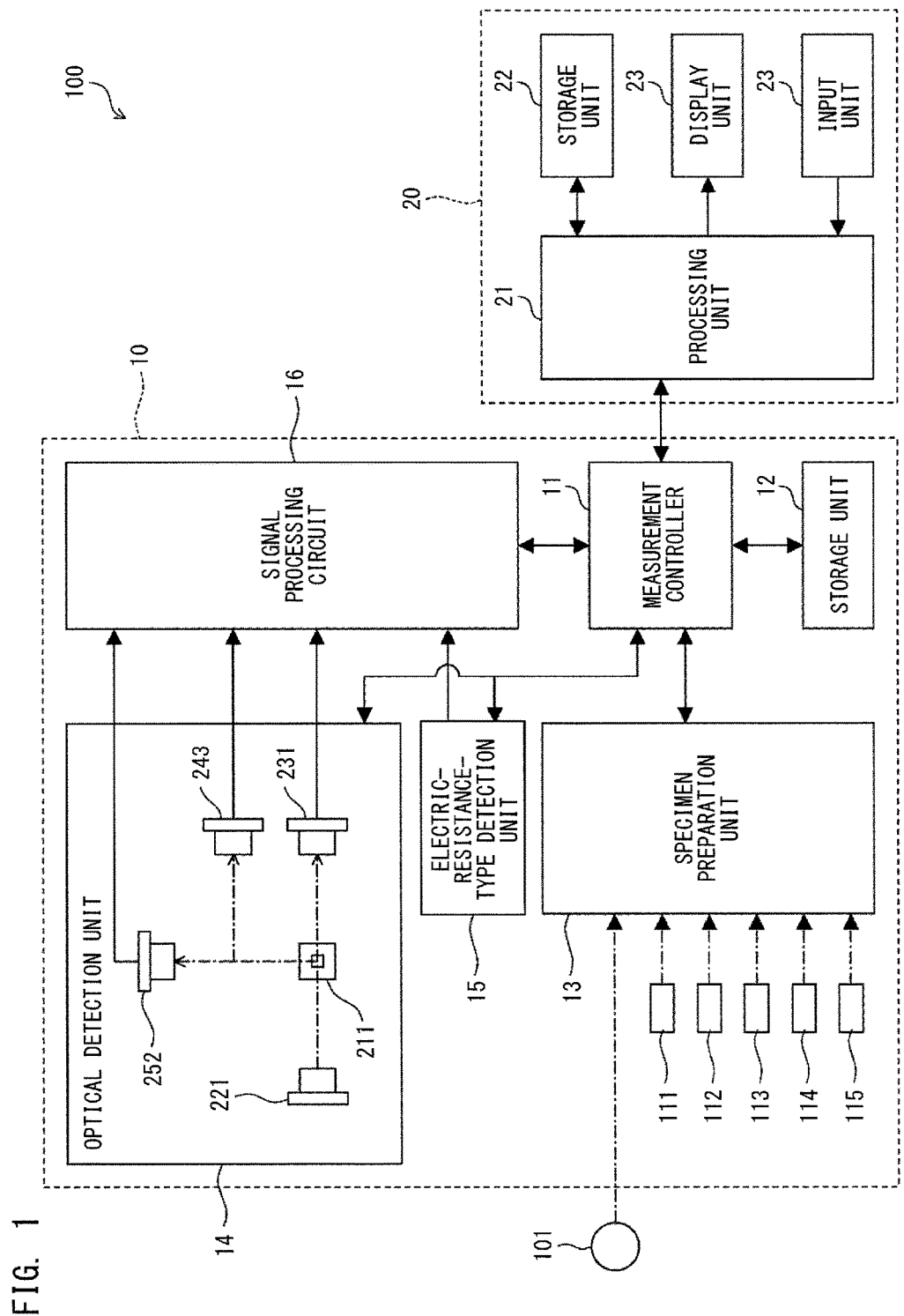
FIG. 1 is a block diagram showing a configuration of a blood analyzer according to Embodiment 1.

As shown in FIG. 1, a blood analyzer 100 includes a measurement unit 10 and an information processing unit 20. The measurement unit 10 includes a measurement controller 11, a storage unit 12, a specimen preparation unit 13, an optical detection unit 14, an electric-resistance-type detection unit 15, and a signal processing circuit 16. The information processing unit 20 includes a processing unit 21, a storage unit 22, a display unit 23, and an input unit 24.

The measurement controller 11 is a CPU, for example. The measurement controller 11 receives signals outputted by components of the measurement unit 10 and controls the components of the measurement unit 10. The measurement controller 11 performs communication with the information processing unit 20. The storage unit 12 is a ROM, a RAM, a hard disk, and the like. The measurement controller 11 executes processes on the basis of programs stored in the storage unit 12.

Containers respectively containing a diluent 111, a hemolyzing agent 112, a fluorescence-labeled antibody reagent 113, a hemolyzing agent 114, and a staining solution 115 are connected to the specimen preparation unit 13. The diluent 111 is also used as a sheath liquid for causing a measurement specimen to flow in a flow cell 211 of the optical detection unit 14 and in a flow cell of the electric-resistance-type detection unit 15.

The hemolyzing agent 112 hemolyzes red blood cells. The hemolyzing agent 112 contains 0.94 mM of lauryltrimethylammonium chloride, 0.13 mM of stearyltrimethylammonium chloride, 0.13 g of BO-20SV, 5 mM of citric acid (anhydrous), 5 mM of trisodium citrate dihydrate (pH7.0), an appropriate amount (300 mOsm) of NaCl, and 1 L of purified water.

The fluorescence-labeled antibody reagent 113 labels a surface antigen on blood cells. The fluorescence-labeled antibody reagent 113 contains: a fluorescent dye that emits fluorescence having a predetermined wavelengths when the fluorescent dye is excited by light emitted from a light source unit 221 described later; and an antibody that binds to the surface antigen on blood cells. The antibody contained in the fluorescence-labeled antibody reagent 113 binds to the surface antigen on blood cells, whereby the surface antigen on blood cells is labelled. The antibody contained in the fluorescence-labeled antibody reagent 113 of Embodiment 1 is an antibody that binds to CD4 antigen. Thus, in Embodiment 1, CD4 antigen expressed on the surfaces of CD4-positive T-cells is labeled by the fluorescence-labeled antibody reagent 113.

The hemolyzing agent 114 hemolyzes red blood cells. The hemolyzing agent 114 contains 34.1 mM of lauryltrimethylammonium chloride, 1.7 mM of stearyltrimethylammonium chloride, 1.0 g/L of EDTA-2K, 20 mM of pH5.0 phosphate buffer, an appropriate amount of NaCl, and 1 L of purified water. The staining solution 115 does not stain red blood cells, which do not have nucleus, but stains plasmodium nucleic acid.

The specimen preparation unit 13 receives a blood sample 101 which is peripheral blood collected from a patient. The specimen preparation unit 13 mixes the blood sample 101, the diluent 111, the hemolyzing agent 112, and the fluorescence-labeled antibody reagent 113 together, to prepare a first measurement specimen to be used in first measurement. In preparation of the first measurement specimen, red blood cells contained in the blood sample 101 are hemolyzed, and the surface antigen on CD4-positive T-cells contained in the blood sample 101 is labeled. The specimen preparation unit 13 mixes the blood sample 101, the diluent 111, the hemolyzing agent 114, and the staining solution 115 together, to prepare a second measurement specimen to be used in second measurement. In preparation of the second measurement specimen, cell membranes of red blood cells contained in the blood sample 101 are partially lysed, and the plasmodium nucleic acid in malaria-infected red blood cells are stained by the staining solution 115. The specimen preparation unit 13 mixes the blood sample 101 and the diluent 111 to prepare a third measurement specimen to be used in third measurement.

In preparation of the first measurement specimen, the hemolyzing agent 114 may be mixed instead of the hemolyzing agent 112 after the dilution ratio by the diluent 111 is changed. Also in this case, red blood cells contained in the blood sample 101 can be hemolyzed. However, using the hemolyzing agent 114 as described above can further increase the accuracy in the first measurement, and thus, in preparation of the first measurement specimen, it is preferable to use the hemolyzing agent 114, not the hemolyzing agent 112.

The first and second measurement specimens are each sent to the optical detection unit 14 through a flow path. The third measurement specimen is sent to the electric-resistance-type detection unit 15 through a flow path.

The optical detection unit 14 performs the first measurement on the basis of the first measurement specimen and the second measurement on the basis of the second measurement specimen, through flow cytometry. The optical detection unit 14 includes the flow cell 211, the light source unit 221, and light receivers 231, 243, 252. In the flow cell 211, the first measurement specimen is caused to flow during the first measurement, and the second measurement specimen is caused to flow during the second measurement.

The light source unit 221 emits light to the first measurement specimen flowing in the flow cell 211 during the first measurement, and emits light to the second measurement specimen flowing in the flow cell 211 during the second measurement. When the first measurement specimen is irradiated with the light from the light source unit 221, first scattered light, second scattered light, and first fluorescence occur from each blood cell in the first measurement specimen. When the second measurement specimen is irradiated with light from the light source unit 221, third scattered light, fourth scattered light, and second fluorescence occur from each blood cell in the second measurement specimen. In the first measurement, the light receivers 231, 243, 252 receive first scattered light, second scattered light, and first fluorescence, respectively. In the second measurement, the light receivers 231, 243, 252 receive third scattered light, fourth scattered light, and second fluorescence, respectively. Each of the light receivers 231, 243, 252 outputs a signal based on the received light, to the signal processing circuit 16. Detailed configuration of the optical detection unit 14 will be described later with reference to FIG. 2.

The electric-resistance-type detection unit 15 performs the third measurement on the basis of the third measurement specimen by a sheath flow DC detection method. The electric-resistance-type detection unit 15 applies voltage to the third measurement specimen flowing in the flow cell of the electric-resistance-type detection unit 15, and catches change in voltage caused by passage of each blood cell, thereby detecting the blood cell. The electric-resistance-type detection unit 15 outputs a detection signal to the signal processing circuit 16.

On the basis of the signal outputted from each of the light receivers 231, 243, 252, the signal processing circuit 16 extracts a waveform that corresponds to the blood cell, and calculates the peak value, the width, the area, and the like of the waveform. The signal processing circuit 16 outputs to the measurement controller 11 the peak values of the waveforms obtained from the signals based on the first scattered light, the second scattered light, the third scattered light, the fourth scattered light, the first fluorescence, and the second fluorescence, as first scattered light information, second scattered light information, third scattered light information, fourth scattered light information, first fluorescence information, and second fluorescence information, respectively. On the basis of the signal outputted from the electric-resistance-type detection unit 15, the signal processing circuit 16 extracts a waveform that corresponds to the blood cell and outputs the peak value of the waveform as blood cell information to the measurement controller 11.

The measurement controller 11 stores in the storage unit 12 information outputted from the signal processing circuit 16 during the first to third measurements. When the first to third measurements end, the measurement controller 11 transmits, as measurement data, the information stored in the storage unit 12 to the information processing unit 20.

The processing unit 21 is a CPU, for example. The processing unit 21 receives signals outputted by components of the information processing unit 20, and controls the components of the information processing unit 20. The processing unit 21 performs communication with the measurement unit 10. The storage unit 22 is a ROM, a RAM, a hard disk, and the like. The processing unit 21 executes processes on the basis of programs stored in the storage unit 22.

The processing unit 21 uses the first scattered light information and the second scattered light information, to classify blood cells contained in the first measurement specimen into at least lymphocyte, monocyte, and granulocyte, and count them. The processing unit 21 uses the first fluorescence information and the second scattered light information, to identify and count CD4-positive T-cells in the first measurement specimen. The processing unit 21 uses the first fluorescence information and the second scattered light information, to identify and count eosinophils in the first measurement specimen. Granulocytes include neutrophils and eosinophils, and thus, on the basis of the granulocyte identification and the eosinophil identification, the processing unit 21 identifies and counts neutrophils in the first measurement specimen. The processing unit 21 uses the third scattered light information and the second fluorescence information, to count malaria-infected red blood cells in the second measurement specimen. The processing unit 21 uses the blood cell information to count red blood cells and platelets in the third measurement specimen. The details of the process to be performed by the processing unit 21 will be described later with reference to FIG. 3.

The display unit 23 is a display on which to display information, and the input unit 24 is a mouse or a keyboard. The processing unit 21 stores measurement results in the storage unit 22 and displays the measurement results on the display unit 23. The processing unit 21 receives instructions from an operator via the input unit 24.

Figure 2:
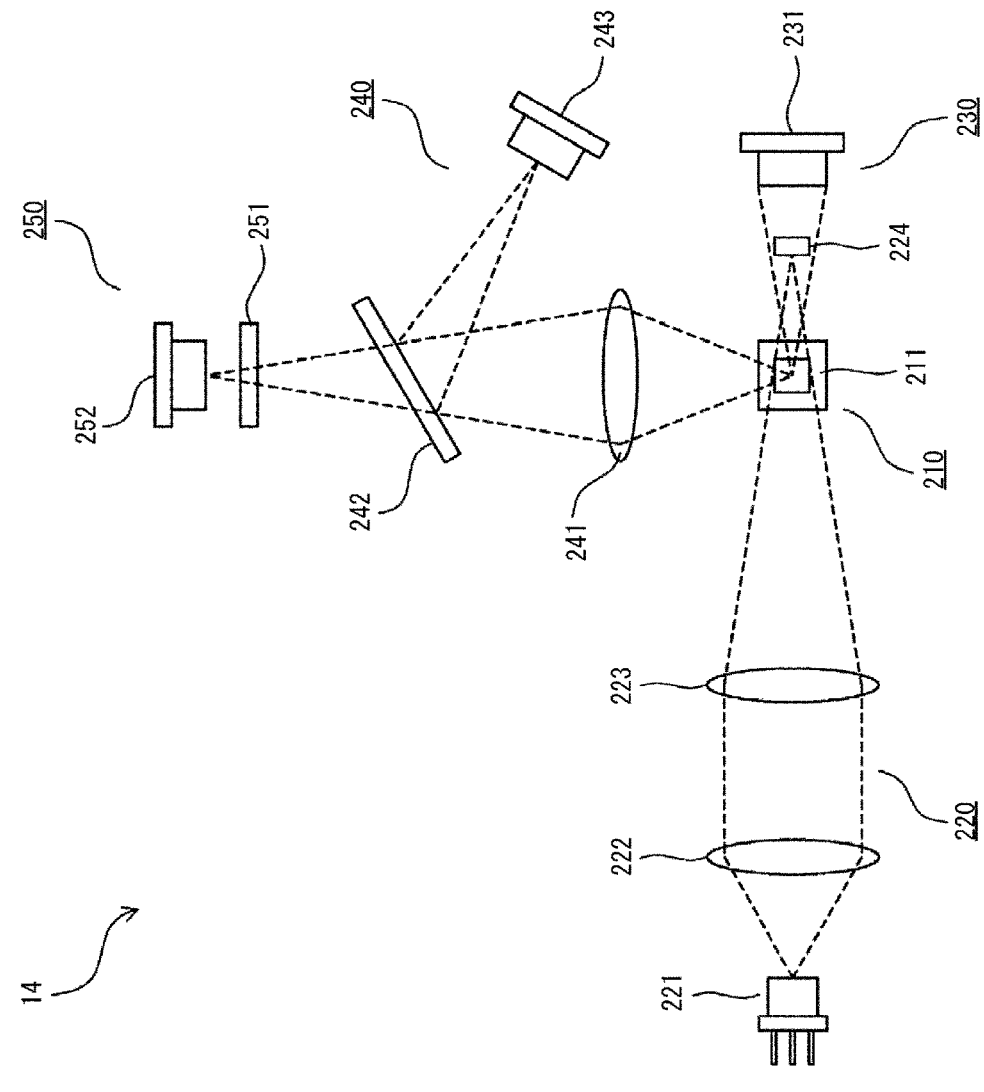
FIG. 2 is a schematic diagram showing a configuration of an optical detection unit according to Embodiment 1.

As shown in FIG. 2, the optical detection unit 14 includes a sheath flow system 210, a beam spot forming system 220, a forward scattered light receiving system 230, a side scattered light receiving system 240, and a fluorescence receiving system 250. The configuration of the optical system of the optical detection unit 14 may be changed as appropriate other than the configuration shown in FIG. 2.

The sheath flow system 210 includes the flow cell 211. The flow cell 211 is formed in a tube shape by means of a translucent material. Each of the first and second measurement specimens is caused to flow in the flow cell 211, while being surrounded by the sheath liquid. Particles contained in each of the first and second measurement specimens pass through the flow cell 211, while being aligned in one line.

The beam spot forming system 220 is configured such that light emitted from the light source unit 221 passes a collimator lens 222 and a condenser lens 223 to be emitted to each of the first and second measurement specimens which is flowing in the flow cell 211. The light source unit 221 is a semiconductor laser light source. Light emitted from the light source unit 221 is laser light in the range of blue light wavelengths. The wavelength of light emitted from the light source unit 221 is set to be not less than 400 nm and not greater than 435 nm. In Embodiment 1, the wavelength of light emitted from the light source unit 221 is about 405 nm.

As described above, when the first measurement specimen is irradiated with light, first scattered light, second scattered light, and first fluorescence occur from each blood cell in the first measurement specimen. When the second measurement specimen is irradiated with light, third scattered light, fourth scattered light, and second fluorescence occur from each blood cell in the second measurement specimen. In Embodiment 1, the first and third scattered light is forward scattered light, and the second and fourth scattered light is side scattered light. Forward scattered light reflects information regarding the size of the particle, side scattered light reflects internal information of the particle, and fluorescence reflects the degree of staining of the particle. Of the light emitted to the flow cell 211, light that has passed through the flow cell 211 without hitting any particle is blocked by a beam stopper 224.

The forward scattered light receiving system 230 is configured such that the first and third scattered light is received by the light receiver 231. The light receiver 231 is a photodiode. The light receiver 231 outputs an electric signal that corresponds to the intensity of each of the received first and third scattered light. The side scattered light receiving system 240 is configured such that second and fourth scattered light is collected by a side condenser lens 241, and is reflected by a dichroic mirror 242, to be received by the light receiver 243. The light receiver 243 is a photodiode. The light receiver 243 outputs an electric signal that corresponds to the intensity of each of the received second and fourth scattered light.

The fluorescence receiving system 250 is configured such that first and second fluorescence that has been collected by the side condenser lens 241 and that has passed through the dichroic mirror 242 is received by the light receiver 252 through a spectral filter 251. Fluorescence occurring from each of the first and second measurement specimens is received by the light receiver 252. Specifically, intrinsic fluorescence occurring from each eosinophil, fluorescence caused by the fluorescence-labeled antibody reagent 113, and fluorescence caused by the staining solution 115 each pass through the dichroic mirror 242 and the spectral filter 251 to be received by the light receiver 252. The light receiver 252 is an avalanche photodiode. The light receiver 252 outputs an electric signal that corresponds to the intensity of the received fluorescence.

Next, the process to be performed by the blood analyzer 100 will be described with reference to the flow chart shown in FIG. 3.

Figure 3:
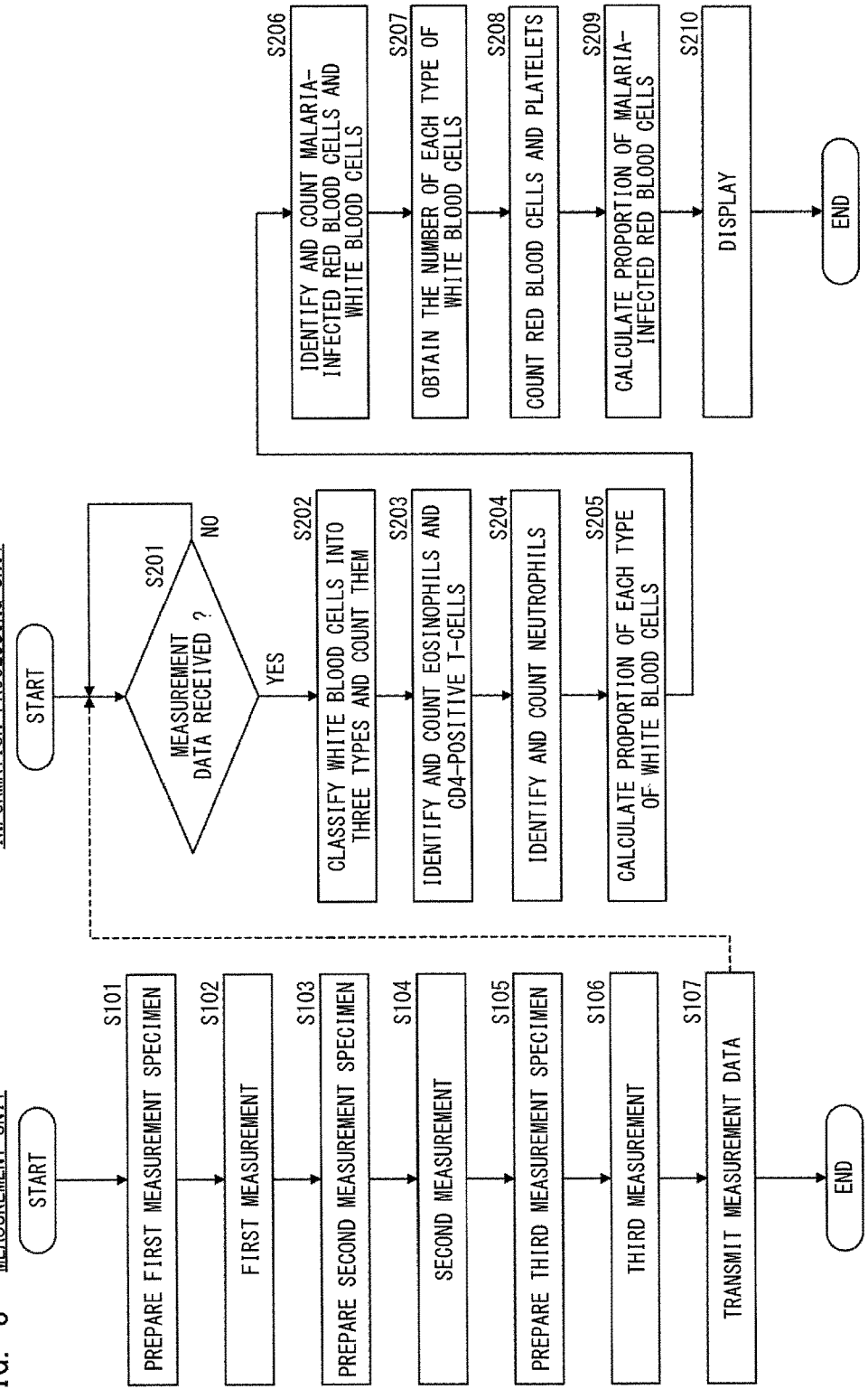
FIG. 3 is a flow chart showing a process performed by the blood analyzer according to Embodiment 1.

As shown in FIG. 3, in steps S101 to S106, the measurement controller 11 controls the specimen preparation unit 13 to prepare a measurement specimen, and controls the optical detection unit 14 and the electric-resistance-type detection unit 15 to perform measurement. Specifically, a first measurement specimen is prepared in step S101, and first measurement is performed by the optical detection unit 14 in step S102. A second measurement specimen is prepared in step S103, and second measurement is performed by the optical detection unit 14 in step S104. A third measurement specimen is prepared in step S105, and third measurement is performed by the electric-resistance-type detection unit 15 in step S106. First to fourth scattered light information and first and second fluorescence information obtained through the first to third measurements are stored in the storage unit 12 of the measurement unit 10.

In step S107, the measurement controller 11 transmits to the information processing unit 20 the information obtained through the first to third measurements, as measurement data. In step S201, upon receiving the measurement data from the measurement unit 10, the processing unit 21 executes the processes in step S202 and thereafter.

In step S202, the processing unit 21 classifies white blood cells into three types, i.e., lymphocyte, monocyte, and granulocyte, and counts them. Specifically, on the basis of the first scattered light information and the second scattered light information, the processing unit 21 creates a scattergram 310 shown in FIG. 4A, and sets regions 311 to 313 on the scattergram 310. In the scattergram 310, the vertical axis represents first scattered light information, and the horizontal axis represents second scattered light information. The regions 311 to 313 are the regions respectively considered as including lymphocytes, monocytes, and granulocytes.

Subsequently, the processing unit 21 classifies the particles included in the regions 311 to 313 as lymphocyte, monocyte, and granulocyte, respectively. By counting the particles included in the respective regions 311 to 313, the processing unit 21 obtains the numbers of lymphocytes monocytes, and granulocytes. By totaling the numbers of lymphocytes monocytes, and granulocytes, the processing unit 21 obtains the number of white blood cells.

For convenience of explanation, in step S202, the scattergram 310 is created and the regions 311 to 313 are set on the scattergram 310. However, the scattergram 310 and the regions 311 to 313 are not always needed to be created, and the particles included in the regions 311 to 313 may be classified and counted through data processing.

This also applies to processes described later. That is, also in step S203, a scattergram 320 and regions 321 and 322 are not always needed to be created, and the particles included in the regions 321 and 322 may be classified and counted through data processing. Also in step S206, a scattergram 330 and regions 331 to 333 are not always needed to be created, and the particles in the regions 331 to 333 may be classified and counted through data processing. Also in step S211 of Embodiment 2 described later, a scattergram 320 and regions 321 and 322 shown in FIG. 7B are not always needed to be created, the particle s included in the regions 321 and 322 may be classified and counted through data processing.

In step S202, a scattergram may be created that has first scattered light information, second scattered light information, and fluorescence information, as three axes. With this, the regions which are respectively considered as including lymphocytes, monocytes, and granulocytes and are set in step S202, and the regions which are respectively considered as including eosinophils and CD4-positive T-cells and are set in step S203 described later can be set on a single scattergram.

In step S203, the processing unit 21 identifies and counts eosinophils and CD4-positive T-cells. Specifically, on the basis of the second scattered light information and the first fluorescence information, the processing unit 21 creates the scattergram 320 shown in FIG. 4B, and sets the regions 321 and 322 on the scattergram 320. In the scattergram 320, the vertical axis represents second scattered light information and the horizontal axis represents first fluorescence information. The regions 321 and 322 are the regions respectively considered as including eosinophils and CD4-positive T-cells.

Here, each eosinophil emits intrinsic fluorescence. Thus, the particles corresponding to eosinophils are distributed on the scattergram 320 at positions having greater fluorescence values than the other particles. The surface antigen on CD4-positive T-cells has been labeled by the fluorescence-labeled antibody reagent 113 during preparation of the first measurement specimen. Thus, the CD4-positive T-cells are also distributed on the scattergram 320 at positions having greater fluorescence values than the other particles. Between eosinophils and CD4-positive T-cells, the value that reflects the internal information of the particle, i.e., the value of the second scattered light information, is different. Thus, the region 321 corresponding to eosinophils and the region 322 corresponding to CD4-positive T-cells can be set in the scattergram 320. The vertical axis of the scattergram 320 represents second scattered light information, but may represent information regarding particle size, i.e., first scattered light information.

Subsequently, the processing unit 21 classifies the particles included in the regions 321 and 322 as eosinophil and CD4-positive T-cell, respectively. By counting the particles included the respective regions 321 and 322, the processing unit 21 obtains the numbers of eosinophils and CD4-positive T-cells, respectively.

As described above, identification and counting of lymphocytes, monocytes, and granulocytes, and identification and counting of eosinophils and CD4-positive T-cells can be performed in a single measurement. That is, the classification and counting of these blood cells can be performed on the basis of optical information obtained while the first measurement specimen is flowing in the flow cell 211 once. Therefore, the classification and counting can be performed quickly.

As described above, the first measurement specimen is prepared from a blood sample 101 by the specimen preparation unit 13, and the prepared first measurement specimen is measured by the optical detection unit 14. Thus, in order to identify and count CD4-positive T-cells, complicated pretreatment is not necessary, and thus, the identification and counting of CD4-positive T-cells can be performed at low cost and in a short time. Since pretreatment by an operator is not necessary, variation in the results of the identification and counting of CD4-positive T-cells can be suppressed.

In order to obtain the number of CD4-positive T-cells, it is not necessary to prepare an apparatus for obtaining the number of white blood cells, and an apparatus for obtaining the proportion of CD4-positive T-cells, individually. That is, it is not necessary to obtain the number of CD4-positive T-cells by multiplying the number of white blood cells obtained by the apparatus for obtaining the number of white blood cells, with the proportion of CD4-positive T-cells obtained by the apparatus for obtaining the proportion of CD4-positive T-cells. With the blood analyzer 100, it is possible to obtain the number of CD4-positive T-cells, by using a single apparatus.

It is known that the number of CD4-positive T-cells decreases in an HIV-infected person. Therefore, the number of CD4-positive T-cells that has been obtained can be utilized in diagnosis of infection with HIV and the disease condition thereof. Since CD4-positive T-cells can be accurately identified on the basis of the region 322 shown in FIG. 4B, the number of CD4-positive T-cells that is highly accurate can be obtained. Thus, when the number of CD4-positive T-cells is utilized in diagnosis, the accuracy of diagnosis can be increased. Other than this, also for a disease in which the number of CD4-positive T-cells increases or decreases, the number of CD4-positive T-cells that has been obtained can be utilized in diagnosis.

In step S204, the processing unit 21 identifies and counts neutrophils. Specifically, the processing unit 21 subtracts the identified eosinophils obtained in step S203 from the identified granulocytes obtained in step S202, thereby to identify neutrophils. That is, the processing unit 21 removes the particles regarded as eosinophils in step S203 from the particles on the scattergram 310 that have been regarded as granulocytes in step S202, thereby to set the region considered as including neutrophils on the scattergram 310. The processing unit 21 counts the particles included in the region considered as including neutrophils on the scattergram 310, thereby to obtain the number of neutrophils. The number of neutrophils may be obtained by subtracting the number of eosinophils from the number of granulocytes.

It is known that the number of neutrophils decreases in an HIV-infected person. Therefore, by using the number of neutrophils that has been obtained in addition to the number of CD4-positive T-cells, diagnosis of infection with HIV and the disease condition thereof can be performed in more detail. Other than this, also for a disease in which the number of neutrophils increases or decreases, the number of neutrophils that has been obtained can be utilized in diagnosis.

In step S205, the processing unit 21 calculates the proportions of the respective types of white blood cells, i.e., the proportions among lymphocytes, monocytes, neutrophils, eosinophils, and CD4-positive T-cells. Specifically, the processing unit 21 divides the numbers of lymphocytes, monocytes, neutrophils, and eosinophils obtained in steps S202 to S204, by the number of white blood cells obtained in step S202, thereby to calculate the respective proportions of lymphocytes, monocytes, neutrophil, and eosinophils. The processing unit 21 divides the number of CD4-positive T-cells obtained in step S203, by the number of lymphocytes obtained in step S205, thereby to calculate the proportion of CD4-positive T-cells.

In step S206, the processing unit 21 identifies and counts malaria-infected red blood cells and white blood cells. Specifically, on the basis of the third scattered light information and the second fluorescence information, the processing unit 21 creates the scattergram 330 shown in FIG. 4C, and sets the regions 331 to 333 on the scattergram 330. In the scattergram 330, the vertical axis represents third scattered light information, and the horizontal axis represents second fluorescence information. The regions 331 to 333 are the regions respectively considered as including malaria-infected red blood cells, white blood cells, and ghost. The ghost in the region 333 includes red blood cells not infected with malaria. Subsequently, the processing unit 21 classifies the particles included in the regions 331 and 332, as malaria-infected red blood cell and white blood cell, respectively. The processing unit 21 counts the particles included in the regions 331 and 332, thereby to obtain the numbers of malaria-infected red blood cells and white blood cells.

Since the number of malaria-infected red blood cells can be obtained, it is possible to determine whether a subject has malaria, and to determine whether malaria of a subject on treatment has been completely cured. These determinations can be made also by using the proportion of malaria-infected red blood cells described later. By using the numbers of CD4-positive T-cells and malaria-infected red blood cell, it is possible to diagnose two diseases, i.e., HIV and malaria, from among so-called three major infectious diseases of HIV, tuberculosis, and malaria. Since the measurement on malaria-infected red blood cells can be performed by the detection unit that measures white blood cells, i.e., the optical detection unit 14, the configuration of the blood analyzer 100 can be simplified.

In step S207, the processing unit 21 obtains the numbers of the respective types of white blood cells, i.e., the numbers of lymphocytes, monocytes, neutrophils, eosinophils, and CD4-positive T-cells. Specifically, the processing unit 21 multiplies the number of white blood cells obtained in step S206, with the proportions of lymphocytes, monocytes, neutrophils, and eosinophils obtained in step S205, thereby to calculate the numbers of lymphocytes, monocytes, neutrophils, and eosinophils, respectively. The processing unit 21 multiplies the number of lymphocytes obtained in step S207, with the proportion of CD4-positive T-cells obtained in step S205, thereby to calculate the number of CD4-positive T-cells. The numbers of blood cells obtained in step S207 are to be used in display on a screen 400 described later.

In step S207, by multiplying the number of white blood cells obtained in step S206, with the respective proportions obtained in step S205, the numbers of the respective types of white blood cells are obtained. However, without being limited thereto, the number of white blood cells may be obtained through another measurement performed by using another measurement specimen, and then the number of white blood cells that has been obtained through said another measurement may be used to obtain the numbers of the respective types of white blood cells in step S207.

Said another measurement may be measurement for identifying and counting nucleated red blood cells and white blood cells, for example. In this case, the specimen preparation unit 13 mixes a blood sample 101, another hemolyzing agent, and another staining solution together, to prepare another measurement specimen. In preparation of said another measurement specimen, red blood cells are hemolyzed, and nucleic acid and cell organelles of nucleated red blood cells and white blood cells are stained. Said another measurement specimen is caused to flow in the flow cell 211, similarly to the first and second measurement specimens. On the basis of forward scattered light and fluorescence occurring from blood cells in said another measurement specimen irradiated with light, a scattergram is created. Regions are set on the created scattergram, whereby identification and counting of nucleated red blood cells and white blood cells are performed.

In step S208, on the basis of the blood cell information obtained through the third measurement, the processing unit 21 counts the numbers of red blood cells and platelets, and calculates the hematocrit value.

In step S209, the processing unit 21 calculates the proportion of malaria-infected red blood cells. Specifically, first, the processing unit 21 adjusts the number of malaria-infected red blood cells obtained in step S206 and the number of red blood cells obtained in step S208, to respective values that correspond to the same volume. For example, each of these two numbers is converted into a number of its corresponding type of cells contained in 1 µL of a blood sample 101. Then, the processing unit 21 divides the number of malaria-infected red blood cells obtained through the unit-volume adjustment, by the number of red blood cells obtained through the unit-volume adjustment, thereby to calculate the proportion of malaria-infected red blood cells.

In step S210, the processing unit 21 causes the display unit 23 to display the screen 400 including the number and the like of blood cells obtained through the process performed by the processing unit 21. Then, the process performed by the blood analyzer 100 ends.

Figure 4C:
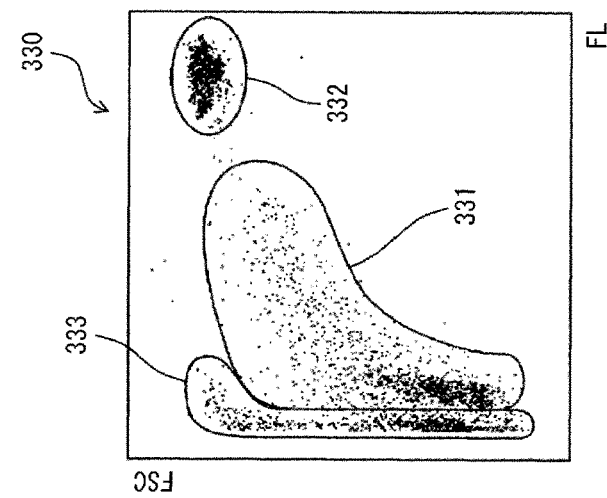
FIG. 4C shows a scattergram based on second measurement according to Embodiment 1.
Figure 4B:
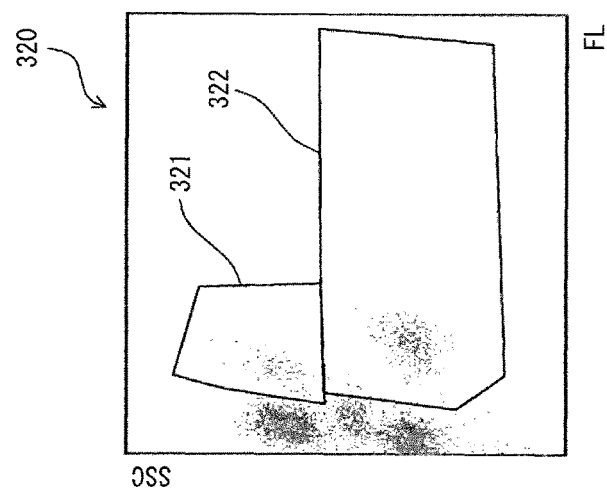
FIG. 4B shows a scattergram based on first measurement according to Embodiment 1.
Figure 4A:
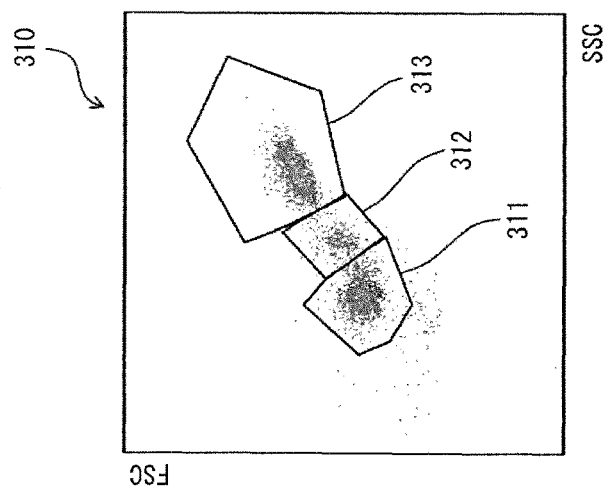
FIG. 4A shows a scattergram based on first measurement according to Embodiment 1.
Figure 5:
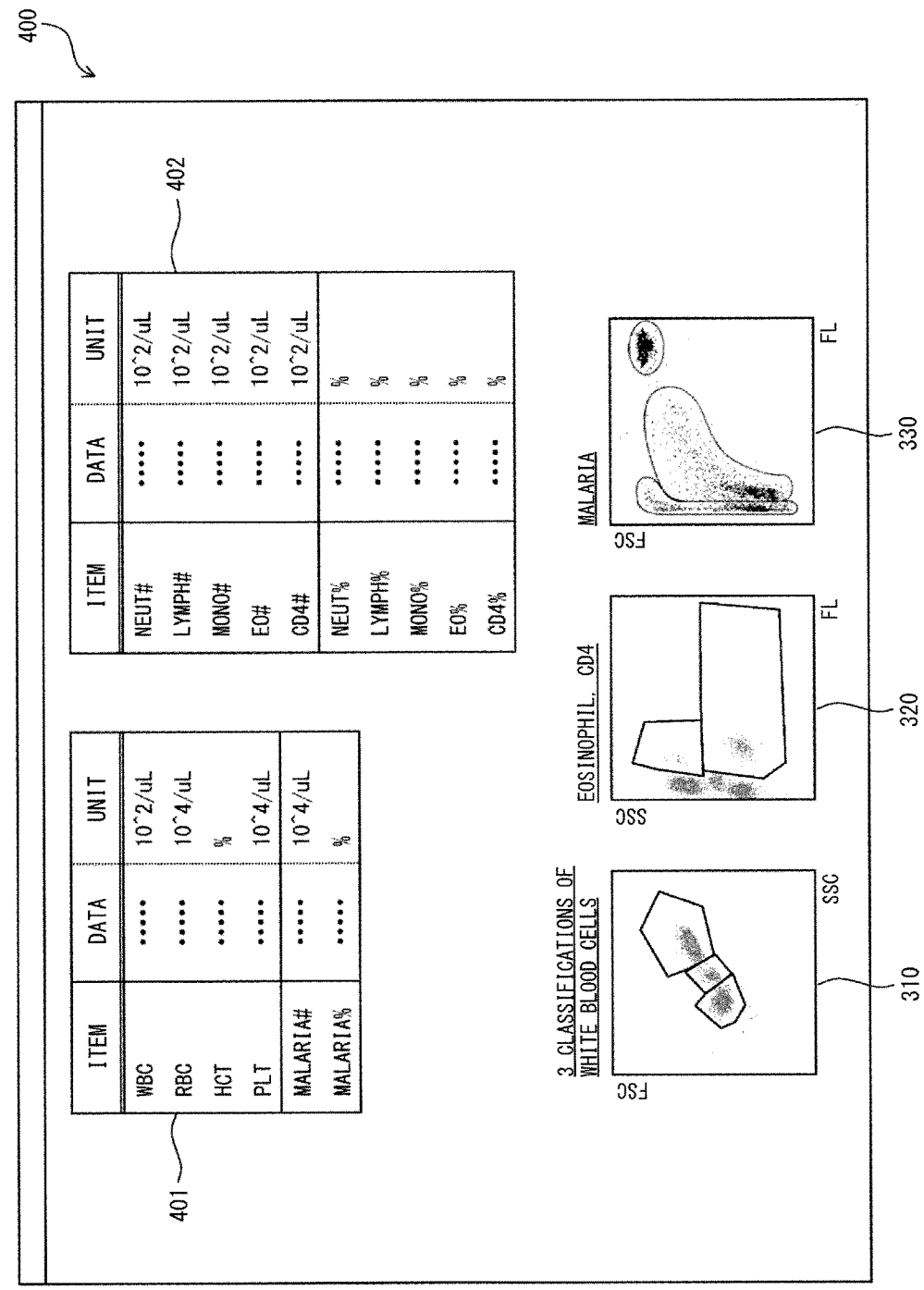
FIG. 5 shows a configuration of a screen displayed on a display unit according to Embodiment 1.

As shown in FIG. 5, the screen 400 includes lists 401 and 402 and the scattergrams 310 to 330 shown in FIGS. 4A to 4C.

In the lists 401 and 402, data expressed in the unit of "10^2/uL" or "10^4/uL" indicates the number of blood cells contained in a predetermined amount of a blood sample 101. The list 401 shows from the top in order: the number of white blood cells obtained in step S206; the number of red blood cells, the hematocrit value, and the number of platelets obtained in step S208; the number of malaria-infected red blood cells obtained in step S206; and the proportion of malaria-infected red blood cells obtained in step S209. The list 402 shows from the top in order: the numbers of neutrophils, lymphocytes, monocytes, eosinophils, and CD4-positive T-cells obtained in step S207; and the proportions of neutrophils, lymphocytes, monocytes, eosinophils, and CD4-positive T-cells obtained in step S205.

The number of white blood cells shown in the list 401 may be the number of white blood cells obtained in step S202. The numbers of lymphocytes, monocytes, neutrophils, eosinophils, and CD4-positive T-cells shown in the list 402 may be the numbers of the respective types of blood cells obtained in steps S202 to S204. However, the number of white blood cells obtained in step S206 and the numbers of the respective types of blood cells obtained in step S207 can be more accurate than the numbers obtained in steps S202 to S204. Therefore, the number of white blood cells shown in the list 401 is preferably the number of white blood cells obtained in step S206 as described above, and the numbers of the respective types of blood cells shown in the list 402 are preferably the numbers of the respective types of blood cells obtained in step S207 as described above.

Since the numbers and the proportions of lymphocytes, monocytes, neutrophils, eosinophils, CD4-positive T-cells, and malaria-infected red blood cells are displayed on the display unit 23, the operator can visually grasp these values. Since these values are displayed on the single screen 400, the operator can smoothly compare the displayed values.

Next, the accuracy of an actually-obtained proportion of CD4-positive T-cells is verified.

In this verification, the proportion of CD4-positive T-cells obtained in Embodiment 1 and the proportion of CD4-positive T-cells obtained in Comparative Example were compared with each other, on the basis of 15 blood samples collected from different subjects. In Comparative Example, each blood sample was pretreated, and the pretreated blood sample was measured by using a general-purpose flow cytometer.

Figure 6:
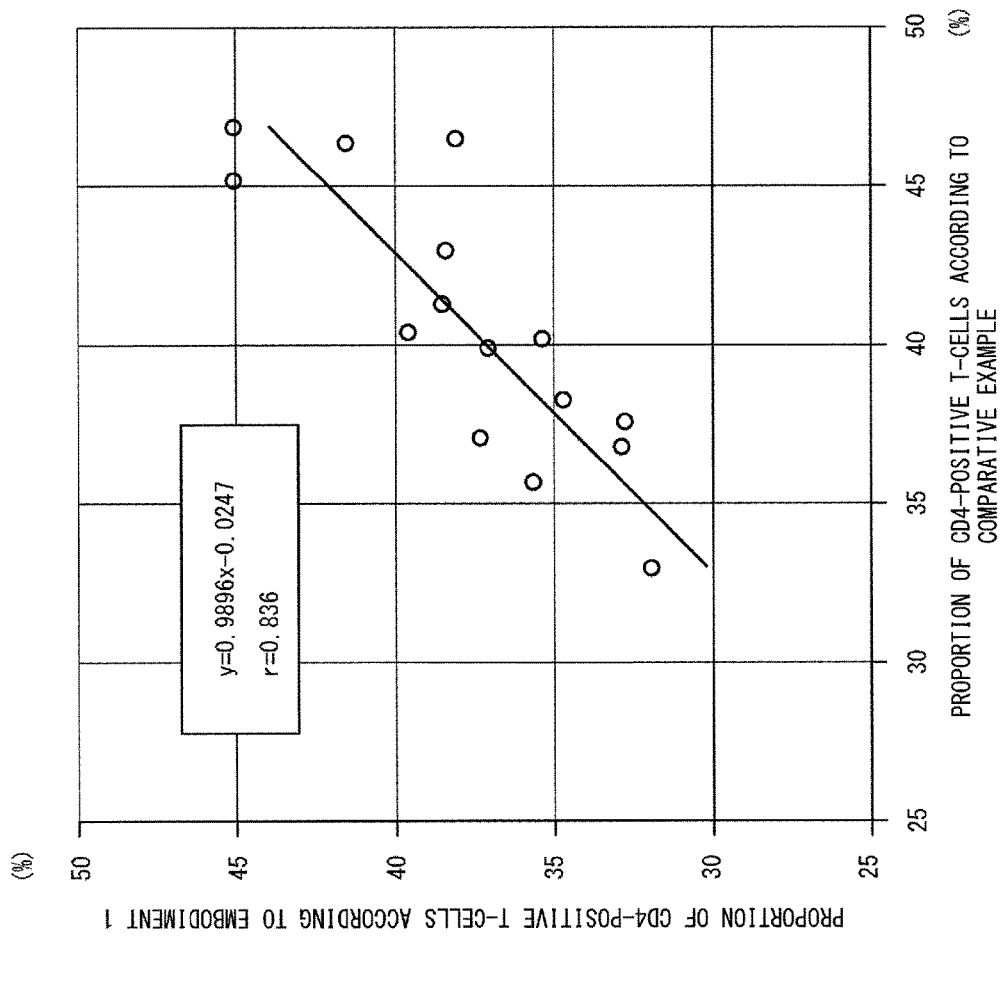
FIG. 6 is a graph for verifying the accuracy of the proportion of CD4-positive T-cells according to Embodiment 1.

The vertical axis shown in FIG. 6 represents proportion of CD4-positive T-cells obtained in Embodiment 1. The horizontal axis shown in FIG. 6 represents proportion of CD4-positive T-cells obtained in Comparative Example. Dots corresponding to the 15 blood samples are plotted on the graph shown in FIG. 6, using the proportion according to Embodiment 1 and the proportion according to Comparative Example as parameters. The graph in FIG. 6 shows an approximate straight line of the dots corresponding to the 15 blood samples. FIG. 6 shows the equation of the approximate straight line with the horizontal axis defined as x and the vertical axis defined as y, and the value of correlation coefficient r between the proportion according to Embodiment 1 and the proportion according to Comparative Example. In each of the cases where the slope of the approximate straight line is closer to 1 and where the value of the correlation coefficient is closer to 1, the correlation between the proportion according to Embodiment 1 and the proportion according to Comparative Example becomes higher, accordingly.

As shown in FIG. 6, the correlation between the proportion according to Embodiment 1 and the proportion according to Comparative Example is high. Therefore, it can be said that the proportion of CD4-positive T-cells according to Embodiment 1 is substantially as accurate as that according to Comparative Example.

Modification of Embodiment 1

In Embodiment 1, the antibody contained in the fluorescence-labeled antibody reagent 113 is an antibody that binds to CD4 antigen. However, without being limited thereto, for example, the antibody contained in the fluorescence-labeled antibody reagent 113 may be an antibody that binds to CD3 antigen, CD8 antigen, CD14 antigen, CD19 antigen, CD45 antigen, or the like.

When the antibody contained in the fluorescence-labeled antibody reagent 113 is an antibody that binds to CD8 antigen, CD8 antigen expressed on the surfaces of CD8-positive T-cells is labeled by the fluorescence-labeled antibody reagent 113. When the first measurement is performed on the basis of the first measurement specimen prepared in this case, the scattergrams 310 and 320 shown in FIGS. 7A and 7B are created. Also in this case, since the regions 311 to 313 and 321 can be set, classification of white blood cells similar to that in Embodiment 1 can be performed. In FIG. 7B, the region 322 is the region considered as including CD8-positive T-cells. Thus, identification and counting of CD8-positive T-cells can be performed.

In general, in accordance with progress of the disease condition of HIV, the ratio of the number of CD4-positive T-cells to the number of CD8-positive T-cells changes. Therefore, the number of CD8-positive T-cells that has been obtained can be utilized in diagnosis of infection with HIV and the disease condition thereof. In addition, since CD8-positive T-cells can be accurately identified on the basis of the region 322 shown in FIG. 7B, the number of CD8-positive T-cells that is highly accurate can be obtained. Accordingly, when utilizing the number of CD8-positive T-cells in diagnosis, the accuracy of the diagnosis can be increased. A case where the ratio of the number of CD4-positive T-cells to the number of CD8-positive T-cells is obtained through a single measurement will be described later in Embodiment 2.

When the antibody contained in the fluorescence-labeled antibody reagent 113 is an antibody that binds to CD19 antigen, CD19 antigen expressed on the surfaces of CD19-positive B cells is labeled by the fluorescence-labeled antibody reagent 113. Also in this case, as in Embodiment 1, on the basis of the regions 311 to 313 and 321 of the scattergrams 310 and 320, classification of white blood cells can be performed. In addition, since the region 322 that includes CD19-positive B cells can be set on the scattergram 320, identification and counting of CD19-positive B cells can be performed.

A CD19-positive B cell is a cell that produces an antibody, and the more the CD19-positive B cells exist, the more immunoglobulin is produced. Thus, it can be said that the number of CD19-positive B cells has clinical significance. Therefore, the number of CD19-positive B cells that has been obtained can be utilized in diagnosis of disease condition.

Other than this, also in each case where the antibody contained in the fluorescence-labeled antibody reagent 113 is an antibody that binds to CD3 antigen, CD14 antigen, or CD45 antigen, classification and counting of blood cells can be performed as shown in FIGS. 7C and 7D and FIGS. 8A to 8D.

When the antibody contained in the fluorescence-labeled antibody reagent 113 is an antibody that binds to CD3 antigen, CD3 antigen expressed on the surfaces of CD3-positive T-cells is labeled by the fluorescence-labeled antibody reagent 113. When the first measurement is performed on the basis of the first measurement specimen prepared in this case, the scattergrams 310 and 320 shown in FIGS. 7C and 7D are created. Also in this case, since the regions 311 to 313 and 321 can be set, classification of white blood cells similar to that in Embodiment 1 can be performed. In FIG. 7D, the region 322 is the region considered as including CD3-positive T-cells. Thus, identification and counting of CD3-positive T-cells can be performed.

Figure 8A:
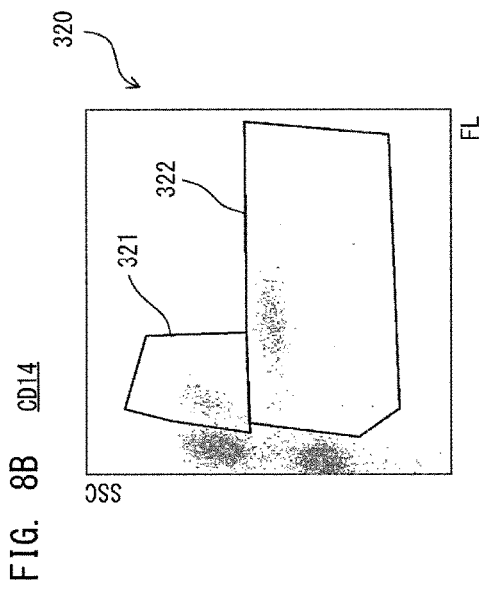
FIG. 8A shows a scattergram based on the first measurement according to Modification of Embodiment 1.
Figure 8B:
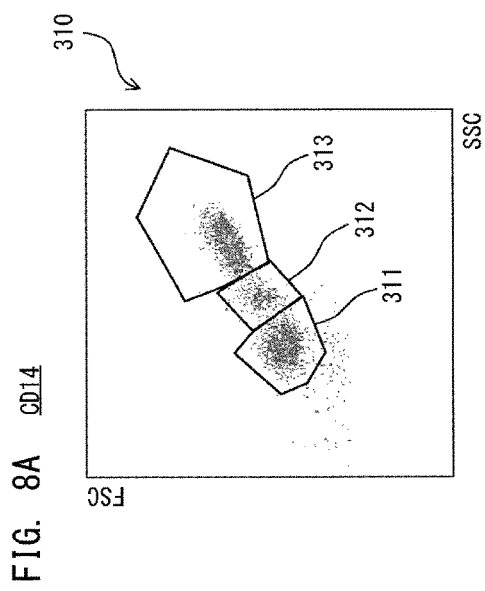
FIG. 8B shows a scattergram based on the first measurement according to Modification of Embodiment 1.

When the antibody contained in the fluorescence-labeled antibody reagent 113 is an antibody that binds to CD14 antigen, CD14 antigen expressed on the surfaces of monocytes is labeled by the fluorescence-labeled antibody reagent 113. When the first measurement is performed on the basis of the first measurement specimen prepared in this case, the scattergrams 310 and 320 shown in FIGS. 8A and 8B are created. Also in this case, since the regions 311 to 313 and 321 can be set, classification of white blood cells similar to that in Embodiment 1 can be performed. In FIG. 8B, the region 322 is the region considered as including monocytes. Thus, also by using the scattergram 320, identification and counting of monocytes can be performed.

Figure 8C:
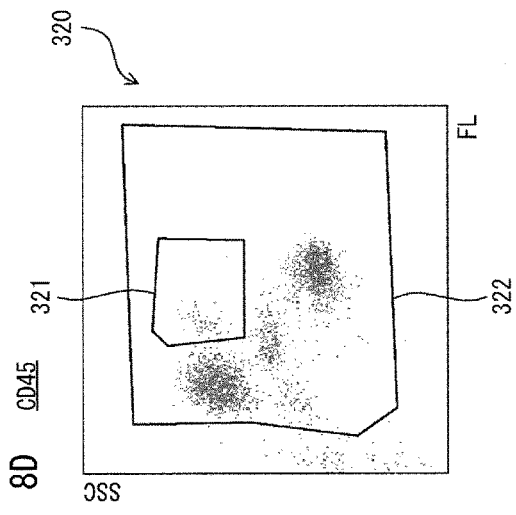
FIG. 8C shows a scattergram based on the first measurement according to Modification of Embodiment 1.
Figure 8D:
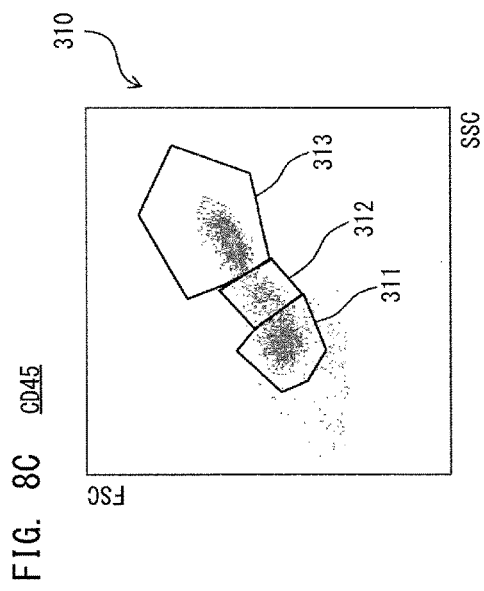
FIG. 8D shows a scattergram based on the first measurement according to Modification of Embodiment 1.

When the antibody contained in the fluorescence-labeled antibody reagent 113 is an antibody that binds to CD45 antigen, CD45 antigen expressed on the surfaces of white blood cells is labeled by the fluorescence-labeled antibody reagent 113. CD45 antigen is a surface antigen that is common to white blood cells. When the first measurement is performed on the basis of the first measurement specimen prepared in this case, the scattergrams 310 and 320 shown in FIGS. 8C and 8D are created. In this case, from each eosinophil, intrinsic fluorescence and fluorescence which is caused by the fluorescence-labeled antibody reagent 113 occur. Thus, the region 321 is shifted to a position having greater first fluorescence values, than in Embodiment 1. Also in this case, since the regions 311 to 313 and 321 can be set, classification of white blood cells similar to that in Embodiment 1 can be performed. In FIG. 8D, the region 322 considered as including white blood cells can be set so as to correspond to the entirety of white blood cells. Thus, also by using the scattergram 320, classification and counting of the entirety of white blood cells can be performed.

Embodiment 2

Figure 9A:
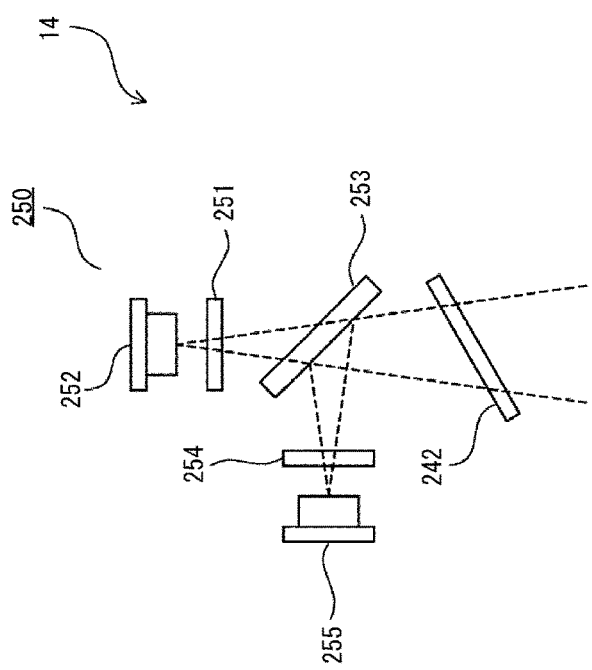
FIG. 9A is a block diagram showing a part of a configuration of a blood analyzer according to Embodiment 2.

As shown in FIG. 9A, in Embodiment 2 when compared with Embodiment 1, a container that contains a fluorescence-labeled antibody reagent 116 is connected to the specimen preparation unit 13. Similar to the fluorescence-labeled antibody reagent 113, the fluorescence-labeled antibody reagent 116 labels a surface antigen on blood cells. The fluorescence-labeled antibody reagent 116 contains: a fluorescent dye that emits fluorescence having a wavelength different from that in the case of the fluorescence-labeled antibody reagent 113 when the fluorescent dye is excited by light emitted from the light source unit 221; and an antibody that binds to the surface antigen on blood cells. The antibody contained in the fluorescence-labeled antibody reagent 116 in Embodiment 2 is an antibody that binds to CD8 antigen. Thus, in Embodiment 2, CD8 antigen expressed on the surfaces of CD8-positive T-cells is labeled by the fluorescence-labeled antibody reagent 116.

The antibody contained in the fluorescence-labeled antibody reagent 116 may be an antibody that binds to an antigen except CD4 antigen and CD8 antigen.

In Embodiment 2, in preparation of the first measurement specimen, the fluorescence-labeled antibody reagent 116 is further mixed. That is, the specimen preparation unit 13 mixes a blood sample 101, the diluent 111, the hemolyzing agent 112, the fluorescence-labeled antibody reagents 113 and 116 together, to prepare a first measurement specimen. Accordingly, in addition to the surface antigen on CD4-positive T-cells contained in the blood sample 101, the surface antigen on CD8-positive T-cells contained in the blood sample 101 is further labeled.

Figure 9B:
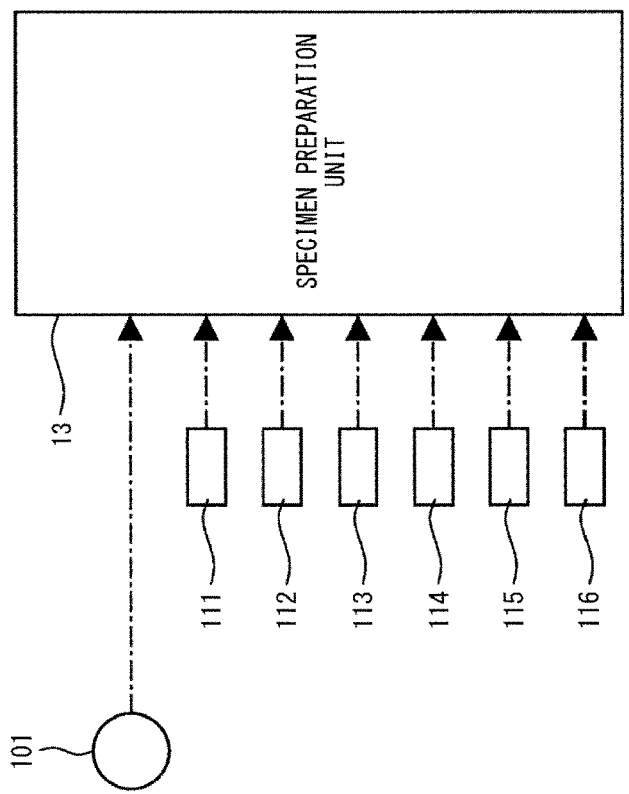
FIG. 9B is a schematic diagram showing a part of a configuration of an optical detection unit according to Embodiment 2.

As shown in FIG. 9B, in Embodiment 2 when compared with Embodiment 1, the fluorescence receiving system 250 of the optical detection unit 14 includes a dichroic mirror 253, a spectral filter 254, and a light receiver 255. Of the first fluorescence that has passed through the dichroic mirror 242, intrinsic fluorescence of each eosinophil and fluorescence caused by the fluorescence-labeled antibody reagent 113 pass through the dichroic mirror 253 to be received by the light receiver 252 as in Embodiment 1. Of the first fluorescence that has passed through the dichroic mirror 242, fluorescence caused by the fluorescence-labeled antibody reagent 116 is reflected by the dichroic mirror 253, and passes through the spectral filter 254 to be received by the light receiver 255. The light receiver 255 is an avalanche photodiode.

As shown in FIG. 10, in the process performed by the blood analyzer 100 in Embodiment 2, step S211 is added after step S204 when compared with Embodiment 1. Hereinafter, only the processes that are different from those in Embodiment 1 will be described.

In step S101, as described above, a blood sample 101, the diluent 111, the hemolyzing agent 112, and the fluorescence-labeled antibody reagents 113 and 116 are mixed together, to prepare a first measurement specimen. In step S102, the first measurement is performed by the optical detection unit 14. At this time, the light receiver 255 outputs a signal based on the received fluorescence to the signal processing circuit 16, and the signal processing circuit 16 outputs to the measurement controller 11 the peak value of the waveform obtained from the signal from the light receiver 255, as third fluorescence information.

In step S211, the processing unit 21 identifies and counts CD8-positive T-cells. Specifically, the processing unit 21 creates a scattergram 320 similar to the scattergram 320 shown in FIG. 7B on the basis of the second scattered light information and the third fluorescence information, and sets regions 321 and 322 on the scattergram 320. In the scattergram 320, the vertical axis represents second scattered light information and the horizontal axis represents third fluorescence information. The regions 321 and 322 are the regions respectively considered as including eosinophils and CD8-positive T-cells. The processing unit 21 classifies the particles included in the region 322 as CD8-positive T-cell and counts the particles included in the region 322, thereby to obtain the number of CD8-positive T-cells.

In step S205, in addition to the proportions of the respective types of blood cells described above, the processing unit 21 calculates the proportion of CD8-positive T-cells. Specifically, by dividing the number of CD8-positive T-cells obtained in step S211 by the number of lymphocytes obtained in step S205, the proportion of CD8-positive T-cells is calculated. In addition, in step S205, the processing unit 21 divides the number of CD4-positive T-cells obtained in step S203, by the number of CD8-positive T-cells obtained in step S211, thereby to calculate the ratio of the number of CD4-positive T-cells to the number of CD8-positive T-cells.

According to Embodiment 2, the ratio of the number of CD4-positive T-cells to the number of CD8-positive T-cells can be calculated by performing only a single measurement on the first measurement specimen. As mentioned above, in accordance with progress of the disease condition of HIV, the ratio of the number of CD4-positive T-cells to the number of CD8-positive T-cells changes. Thus, it is possible to smoothly obtain the ratio of the number of CD4-positive T-cells to the number of CD8-positive T-cells and to utilize the obtained ratio in diagnosis of infection with HIV and progress of the disease condition thereof.

In step S207, in addition to the numbers of the respective types of blood cells described above, the processing unit 21 calculates the number of CD8-positive T-cells. Specifically, the processing unit 21 multiplies the number of lymphocytes obtained in step S207, with the proportion of CD8-positive T-cells obtained in step S205, thereby to obtain the number of CD8-positive T-cells.

Figure 11:
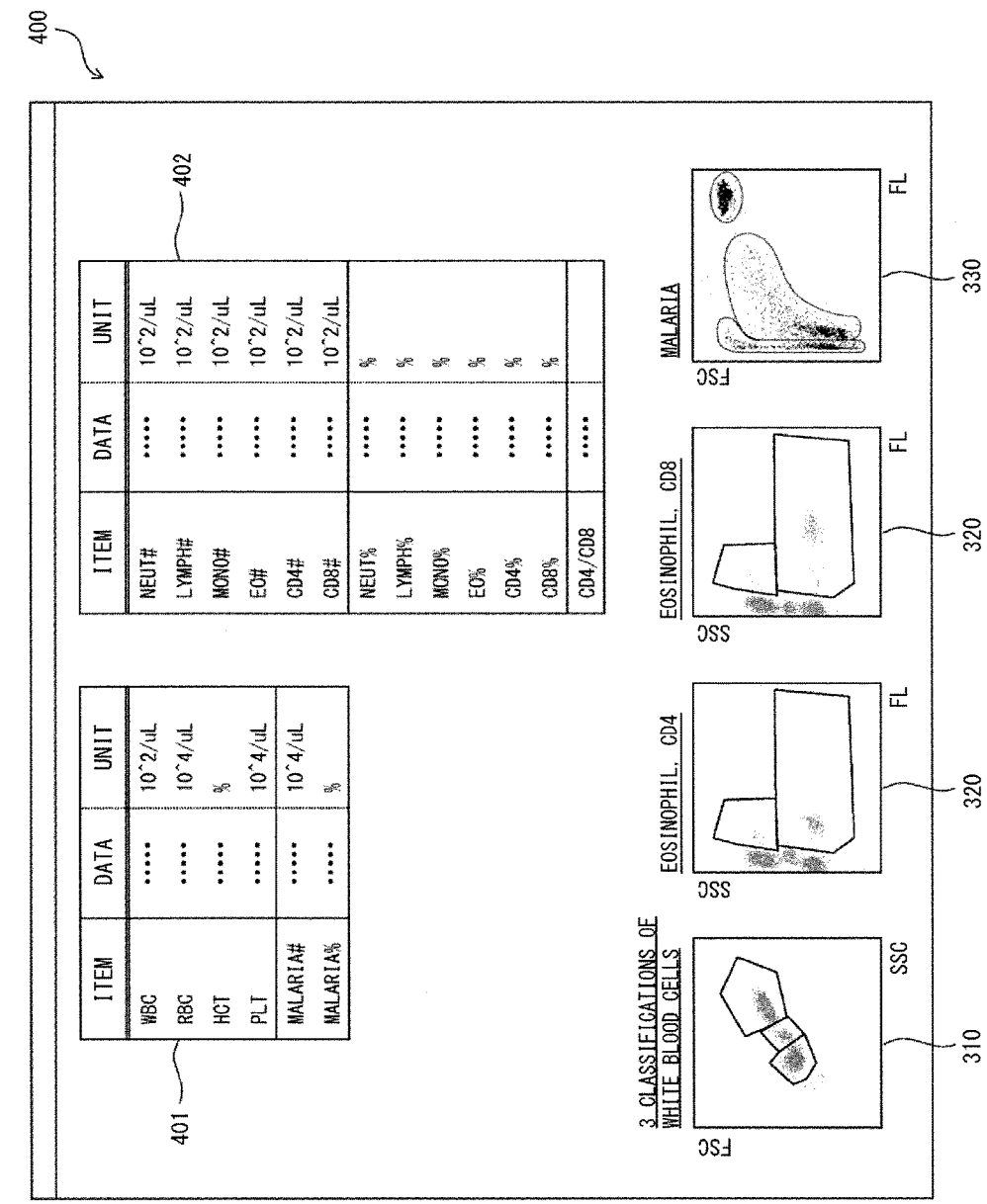
FIG. 11 shows a configuration of a screen displayed on a display unit according to Embodiment 2.

As shown in FIG. 11, when compared with Embodiment 1, the screen 400 in Embodiment 2 further includes the scattergram 320 used in identification and counting of CD8-positive T-cells. When compared with Embodiment 1, the list 402 in Embodiment 2 further shows the number of CD8-positive T-cells, the proportion of CD8-positive T-cells, and the ratio of the number of CD4-positive T-cells to the number of CD8-positive T-cells. With reference to the screen 400 shown in FIG. 11, the operator can visually grasp such values regarding CD8-positive T-cells.

What is claimed is:

1. A blood analyzer comprising:
   a specimen preparation unit configured to mix a blood sample with a hemolyzing agent which hemolyzes red blood cells and with a fluorescence-labeled antibody reagent which labels a predetermined surface antigen on blood cells, to prepare a first measurement specimen;
   a flow cell through which the first measurement specimen prepared by the specimen preparation unit is caused to flow;
   a light source unit configured to emit light to the first measurement specimen flowing in the flow cell;
   light receivers configured to respectively receive first scattered light, second scattered light, and first fluorescence which are derived from blood cells in the first measurement specimen in response to the emission of the light; and
   a processing unit configured to identify and count lymphocytes in the first measurement specimen by using first scattered light information based on the first scattered light and second scattered light information based on the second scattered light, and configured to identify and count blood cells having thereon the predetermined surface antigen in the first measurement specimen by using first fluorescence information based on the first fluorescence, wherein the processing unit is configured to differentiate between eosinophils and cells identified by fluorescent labelled antibody by using second scattered light information based on the second scattered light and the first fluorescence information based on the first fluorescence, and count each of the eosinophils and the cells identified by the fluorescent labelled antibody.

2. The blood analyzer of claim 1, wherein the processing unit further identifies and counts monocytes in the first measurement specimen by using the first scattered light information based on the first scattered light and the second scattered light information based on the second scattered light.

3. The blood analyzer of claim 1, wherein the processing unit further identifies and counts granulocytes in the first measurement specimen by using the first scattered light information based on the first scattered light and the second scattered light information based on the second scattered light.

4. The blood analyzer of claim 1, wherein the first scattered light is forward scattered light, the second scattered light is side scattered light, and the processing unit identifies and counts the blood cells having thereon the predetermined surface antigen in the first measurement specimen by using second scattered light information based on the side scattered light and the first fluorescence information based on the first fluorescence.

5. The blood analyzer of claim 1, wherein the blood cells having thereon the predetermined surface antigen are CD4-positive T-cells.

6. The blood analyzer of claim 1, wherein the blood cells having thereon the predetermined surface antigen are CD8-positive T-cells.

7. The blood analyzer of claim 1, wherein the blood cells having thereon the predetermined surface antigen are CD19-positive B cells.

8. The blood analyzer of claim 1, comprising a display unit configured to display information, wherein the processing unit causes the display unit to display information based on the number of the blood cells having thereon the predetermined surface antigen that have been counted.

9. The blood analyzer of claim 8, wherein the processing unit causes the display unit to display information based on the number of the lymphocytes that have been counted.

10. The blood analyzer of claim 8, wherein
the processing unit causes the display unit to display a screen that includes information based on the number of the blood cells having thereon the predetermined surface antigen that have been counted, and information based on the number of the lymphocytes that have been counted.

11. The blood analyzer of claim 1, wherein
the processing unit further identifies and counts eosinophils in the first measurement specimen by using the first fluorescence information.

12. The blood analyzer of claim 11, wherein
the processing unit counts neutrophils in the first measurement specimen on the basis of counting of granulocytes and counting of eosinophils.

13. The blood analyzer of claim 1, comprising:
a display unit configured to display information, wherein
the specimen preparation unit mixes the blood sample with a hemolyzing agent which hemolyzes red blood cells and with a staining solution which stains plasmodium nucleic acid, to prepare a second measurement specimen,
the light receivers respectively receive third scattered light and second fluorescence which are derived from blood cells in the second measurement specimen in response to emission of the light,
the processing unit identifies and counts malaria-infected red blood cells in the second measurement specimen by using third scattered light information based on the third scattered light and second fluorescence information based on the second fluorescence, and
the processing unit causes the display unit to display a result of the counting of the malaria-infected red blood cells.

14. The blood analyzer of claim 1, wherein
the light source unit emits light whose wavelength is not less than 400 nm and not greater than 435 nm.

* * * * *